(12) United States Patent
Tanioka et al.

(10) Patent No.: US 7,660,626 B2
(45) Date of Patent: Feb. 9, 2010

(54) IONTOPHORESIS DEVICE

(75) Inventors: Akihiko Tanioka, Ohota-ku (JP); Mie Minagawa, Minato-ku (JP); Kiyoshi Kanamura, Hachiouji (JP); Akihiko Matsumura, Shibuya-ku (JP); Mizuo Nakayama, Shibuya-ku (JP); Takehiko Matsumura, Shibuya-ku (JP); Hidero Akiyama, Shibuya-ku (JP)

(73) Assignee: TTI ellebeau, Inc., Tokyo (JP)

( * ) Notice: Subject to any disclaimer, the term of this patent is extended or adjusted under 35 U.S.C. 154(b) by 494 days.

(21) Appl. No.: 11/195,364

(22) Filed: Aug. 2, 2005

(65) Prior Publication Data

US 2006/0173401 A1 Aug. 3, 2006

(30) Foreign Application Priority Data

Feb. 3, 2005 (JP) ............................ 2005-027748

(51) Int. Cl.
*A61N 1/30* (2006.01)
(52) U.S. Cl. ........................................................ 604/20
(58) Field of Classification Search ............. 604/20–21, 604/174, 180
See application file for complete search history.

(56) References Cited

U.S. PATENT DOCUMENTS

| 4,116,889 A | 9/1978 | Chlanda et al. ................ 521/27 |
| 4,140,121 A | 2/1979 | Kuhl et al. .................. 128/260 |
| 4,519,938 A | 5/1985 | Papir ........................... 252/500 |

(Continued)

FOREIGN PATENT DOCUMENTS

CA 2205444 6/1996

(Continued)

OTHER PUBLICATIONS

U.S. Appl. No. 11/471,973, filed Mar. 22, 2007, Akihiko et al.
U.S. Appl. No. 11/475,838, filed Feb. 1, 2007, Matsumura et al.
U.S. Appl. No. 11/617,609, filed Sep. 13, 2007, Carter.
JIS (Japanese Industrial Standards), Testing Methods for Bubble Point of Membrane Filters, K3832, 11 pages, 1990.
Ito et al., "In Vitro Effect of Ion Exchange Membrane on Iontophoresis" Medicine and Biology, 147(3); pp. 41-46, 2003.
Ogata, N., "Dodensei Kobunshi" (Electrically Conductive High Molecular Compounds), Kodansha Scientific, (1990).

*Primary Examiner*—Nicholas D Lucchesi
*Assistant Examiner*—Theodore J Stigell
(74) *Attorney, Agent, or Firm*—Seed IP Law Group PLLC

(57) ABSTRACT

The present invention provides an iontophoresis device with high administration efficient of a drug. An iontophoresis device, including an active electrode structure including: an electrode to which a positive electrical potential is applied; a drug holding part for holding a drug solution containing positively charged drug ions, the drug holding part being placed on a front side of the electrode; a cellulose-based resin film placed on a front side of the drug holding part or a complex film composed of a cation exchange membrane and a cellulose-based resin film placed on a front side of the cation exchange membrane, the complex film being placed on a front side of the drug holding part, in which the drug ions are administered through the cellulose-based resin film.

24 Claims, 3 Drawing Sheets

U.S. PATENT DOCUMENTS

| | | | |
|---|---|---|---|
| 4,722,726 A | 2/1988 | Sanderson et al. | 604/20 |
| 4,731,049 A | 3/1988 | Parsi | 604/20 |
| 4,744,787 A | 5/1988 | Phipps et al. | 604/20 |
| 4,747,819 A | 5/1988 | Phipps et al. | 604/20 |
| 4,915,685 A | 4/1990 | Petelenz et al. | 604/20 |
| 4,927,408 A | 5/1990 | Haak et al. | 604/20 |
| 4,940,456 A * | 7/1990 | Sibalis et al. | 604/20 |
| 5,057,072 A | 10/1991 | Phipps | 604/20 |
| 5,080,646 A | 1/1992 | Theeuwes et al. | 604/20 |
| 5,084,006 A | 1/1992 | Lew et al. | 604/20 |
| 5,084,008 A | 1/1992 | Phipps | 604/20 |
| 5,135,477 A | 8/1992 | Untereker et al. | 604/20 |
| 5,147,296 A | 9/1992 | Theeuwes et al. | 604/20 |
| 5,162,043 A | 11/1992 | Lew et al. | 604/20 |
| 5,169,383 A | 12/1992 | Gyory et al. | 604/20 |
| 5,238,613 A | 8/1993 | Anderson | 264/22 |
| 5,322,502 A | 6/1994 | Theeuwes et al. | 604/20 |
| 5,326,341 A | 7/1994 | Lew et al. | 604/20 |
| 5,395,310 A | 3/1995 | Untereker et al. | 604/20 |
| 5,405,317 A | 4/1995 | Myers et al. | 604/20 |
| 5,496,266 A | 3/1996 | Haak et al. | 604/20 |
| 5,503,632 A | 4/1996 | Haak | 604/20 |
| 5,543,098 A | 8/1996 | Myers et al. | 264/104 |
| 5,573,668 A | 11/1996 | Grosh et al. | 210/490 |
| 5,637,084 A | 6/1997 | Kontturi et al. | 604/20 |
| 5,647,844 A * | 7/1997 | Haak et al. | 604/20 |
| 5,668,170 A | 9/1997 | Gyory | 514/449 |
| 5,711,761 A | 1/1998 | Untereker et al. | 604/20 |
| 5,788,666 A * | 8/1998 | Atanasoska | 604/20 |
| 5,840,056 A | 11/1998 | Atanasoska | 604/20 |
| 5,840,339 A | 11/1998 | Kunin | 424/489 |
| 5,871,460 A | 2/1999 | Phipps et al. | 604/20 |
| 5,894,021 A | 4/1999 | Okabe et al. | 424/449 |
| 5,941,843 A | 8/1999 | Atanasoska et al. | 604/20 |
| 5,993,435 A | 11/1999 | Haak et al. | 604/501 |
| 6,049,733 A | 4/2000 | Phipps et al. | 604/20 |
| 6,064,908 A | 5/2000 | Muller et al. | 604/20 |
| 6,103,078 A | 8/2000 | Hitchems et al. | 204/296 |
| 6,109,852 A | 8/2000 | Shahinpoor et al. | 414/1 |
| 6,169,920 B1 | 1/2001 | Haak et al. | 604/20 |
| 6,256,533 B1 | 7/2001 | Yuzhakov et al. | 604/21 |
| 6,258,276 B1 | 7/2001 | Mika et al. | 210/638 |
| 6,314,317 B1 | 11/2001 | Willis | 604/20 |
| 6,329,488 B1 | 12/2001 | Terry et al. | 528/28 |
| 6,350,259 B1 | 2/2002 | Sage, Jr. et al. | 604/501 |
| 6,377,847 B1 | 4/2002 | Keusch et al. | 604/20 |
| 6,377,848 B1 | 4/2002 | Garde et al. | 604/20 |
| 6,385,488 B1 | 5/2002 | Flower et al. | 604/20 |
| 6,394,994 B1 | 5/2002 | Vilambi et al. | 604/501 |
| 6,402,732 B1 | 6/2002 | Flower et al. | 604/501 |
| 6,405,875 B1 | 6/2002 | Cutler | 210/477 |
| 6,454,941 B1 | 9/2002 | Cutler et al. | 210/266 |
| 6,462,935 B1 | 10/2002 | Shiue et al. | 361/511 |
| 6,468,657 B1 | 10/2002 | Hou et al. | 428/403 |
| 6,497,887 B1 | 12/2002 | Zecchino et al. | 424/401 |
| 6,522,919 B1 | 2/2003 | Flower et al. | 604/20 |
| 6,553,255 B1 | 4/2003 | Miller et al. | 604/20 |
| 6,584,349 B1 | 6/2003 | Sage, Jr. et al. | 604/20 |
| 6,597,947 B1 | 7/2003 | Inoue et al. | 604/20 |
| 6,629,968 B1 | 10/2003 | Jain et al. | 604/501 |
| 6,635,045 B2 | 10/2003 | Keusch et al. | 604/501 |
| 6,678,554 B1 | 1/2004 | Sun et al. | 604/20 |
| 6,678,555 B2 | 1/2004 | Flower et al. | 604/20 |
| 6,743,432 B1 | 6/2004 | Yanai et al. | 424/400 |
| 6,775,569 B2 | 8/2004 | Mori et al. | 604/20 |
| 6,858,018 B1 | 2/2005 | Green et al. | 604/19 |
| 6,862,473 B2 | 3/2005 | Keusch et al. | 604/20 |
| 7,398,121 B2 | 7/2008 | Matsumura et al. | 604/20 |
| 2002/0022795 A1 | 2/2002 | Reynolds et al. | 604/20 |
| 2002/0099320 A1 | 7/2002 | Beck | 604/20 |
| 2003/0065305 A1 | 4/2003 | Higuchi et al. | 604/501 |
| 2003/0088205 A1 | 5/2003 | Chandrasekaran et al. | 604/20 |
| 2003/0168404 A1 | 9/2003 | Mika et al. | 210/639 |
| 2004/0105881 A1 | 6/2004 | Cevc et al. | 424/450 |
| 2004/0138609 A1 | 7/2004 | Fukuta et al. | 604/20 |
| 2004/0167459 A1 | 8/2004 | Higuchi et al. | 604/20 |
| 2005/0011826 A1 | 1/2005 | Childs et al. | 210/490 |
| 2005/0070840 A1 | 3/2005 | Matsumura et al. | 604/20 |
| 2006/0083962 A1 | 4/2006 | Takekawa et al. | 429/13 |
| 2006/0095001 A1 | 5/2006 | Matsumura et al. | 604/20 |
| 2006/0116628 A1 | 6/2006 | Matsumura et al. | 604/20 |
| 2006/0129085 A1 | 6/2006 | Tanioka et al. | 604/20 |
| 2006/0135906 A1 | 6/2006 | Matsumura et al. | 604/20 |
| 2006/0173401 A1 | 8/2006 | Tanioka et al. | 604/20 |
| 2006/0198879 A1 | 9/2006 | Fukuta et al. | 424/448 |
| 2006/0211980 A1 | 9/2006 | Cormier et al. | 604/20 |
| 2006/0217654 A1 | 9/2006 | Matsumura et al. | 604/20 |
| 2006/0276742 A1 | 12/2006 | Matsumura et al. | 604/20 |
| 2007/0021711 A1 | 1/2007 | Matsumura et al. | 604/20 |
| 2007/0027426 A1 | 2/2007 | Matsumura et al. | 604/20 |
| 2007/0060859 A1 | 3/2007 | Kanamura et al. | 604/20 |
| 2007/0060860 A1 | 3/2007 | Nakayama et al. | 604/20 |
| 2007/0066930 A1 | 3/2007 | Tanioka et al. | 604/20 |
| 2007/0066931 A1 | 3/2007 | Kanamura et al. | 604/20 |
| 2007/0071807 A1 | 3/2007 | Akiyama et al. | 424/451 |
| 2007/0073212 A1 | 3/2007 | Matsumura | 604/20 |
| 2007/0078375 A1 | 4/2007 | Smith | 604/20 |
| 2007/0083147 A1 | 4/2007 | Smith | 604/20 |
| 2007/0088332 A1 | 4/2007 | Akiyama | 604/890.1 |
| 2007/0093787 A1 | 4/2007 | Smith | 604/890.1 |
| 2007/0112294 A1 | 5/2007 | Akiyama et al. | 604/20 |
| 2007/0135754 A1 | 6/2007 | Akiyama et al. | 604/20 |
| 2007/0197955 A1 | 8/2007 | Akiyama et al. | 604/20 |
| 2007/0213652 A1 | 9/2007 | Carter | 604/20 |
| 2008/0213646 A1 | 9/2008 | Takekawa et al. | 429/33 |

FOREIGN PATENT DOCUMENTS

| | | | |
|---|---|---|---|
| EP | 0 411 146 A1 | 2/1991 | |
| EP | 0 931 564 A1 | 7/1999 | |
| EP | 1 440 707 | 7/2004 | |
| EP | 1 566 197 A1 | 8/2005 | |
| GB | 2 265 088 | 9/1993 | |
| JP | 52-151720 | 12/1977 | |
| JP | 60-35936 | 2/1985 | |
| JP | 02-206474 | 8/1990 | |
| JP | 03-094771 | 4/1991 | |
| JP | 03-504343 | 9/1991 | |
| JP | 04-297277 | 10/1992 | |
| JP | 05-220385 | 8/1993 | |
| JP | 08-164212 | 6/1996 | |
| JP | 09-201420 | 8/1997 | |
| JP | 2-801083 | 7/1998 | |
| JP | 10-510175 | 10/1998 | |
| JP | 2845509 | 10/1998 | |
| JP | 11-273452 | 10/1999 | |
| JP | 30-40517 | 3/2000 | |
| JP | 2000-229128 | 8/2000 | |
| JP | 2000-229129 | 8/2000 | |
| JP | 2000-237326 | 9/2000 | |
| JP | 2000-237327 | 9/2000 | |
| JP | 2000-237328 | 9/2000 | |
| JP | 2000-237329 | 9/2000 | |
| JP | 2000-288097 | 10/2000 | |
| JP | 2000-288098 | 10/2000 | |
| JP | 2001-505091 | 4/2001 | |
| JP | 2001-120670 | 5/2001 | |
| JP | 2002-233584 | 8/2002 | |
| JP | 2004-188188 * | 7/2004 | |
| JP | 2004-202057 | 7/2004 | |
| JP | 2004-292438 | 10/2004 | |
| JP | 2004-317317 | 10/2004 | |
| JP | 2004-357313 | 12/2004 | |
| JP | 2005-503194 | 2/2005 | |

| | | | | | | |
|---|---|---|---|---|---|---|
| JP | 2006-149891 | 6/2006 | | WO | WO96/17648 | 6/1996 |
| JP | 2006-212194 | 8/2006 | | WO | WO 97/47353 | 12/1997 |
| JP | 2007-037640 | 2/2007 | | WO | WO02/100474 | 12/2002 |
| JP | 2007-050136 | 3/2007 | | WO | 03/008078 | 1/2003 |
| WO | WO 90/03825 | 4/1990 | | WO | WO03/037425 | 5/2003 |
| WO | 90/04433 | 5/1990 | | WO | 2004/073843 | 9/2004 |
| WO | 90/08571 | 8/1990 | | WO | 2006/062108 | 6/2006 |
| WO | 91/16943 | 11/1991 | | | | |

* cited by examiner

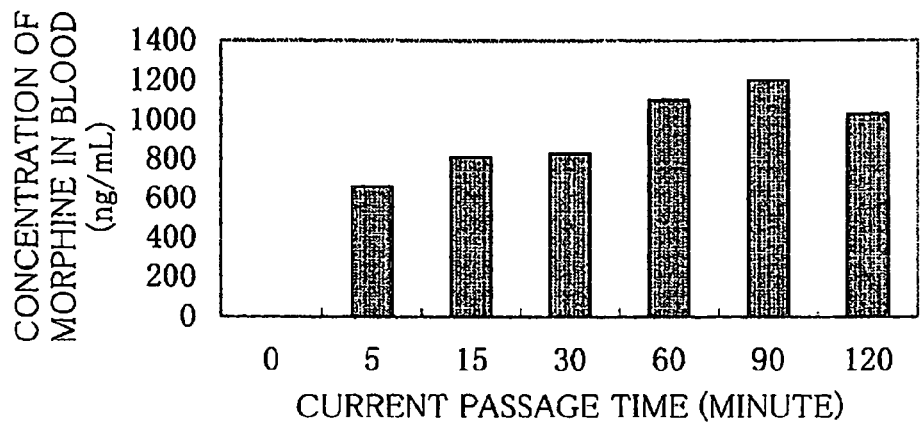
FIG. 3A
|  | ACTIVE ELECTRODE ASSEMBLY | | COUNTER ELECTRODE ASSEMBLY | |
|---|---|---|---|---|
|  | ELECTROLYTE SOLUTION HOLDING PART (12) | DRUG HOLDING PART (14) | ELECTROLYTE SOLUTION HOLDING PART (22) | ELECTROLYTE SOLUTION HOLDING PART (24) |
| BEFORE PASSAGE OF CURRENT | 4.8 | 4.4 | 4.8 | 4.8 |
| AFTER PASSAGE OF CURRENT | 4.7 | 4.7 | 5.0 | 4.7 |
FIG. 3B
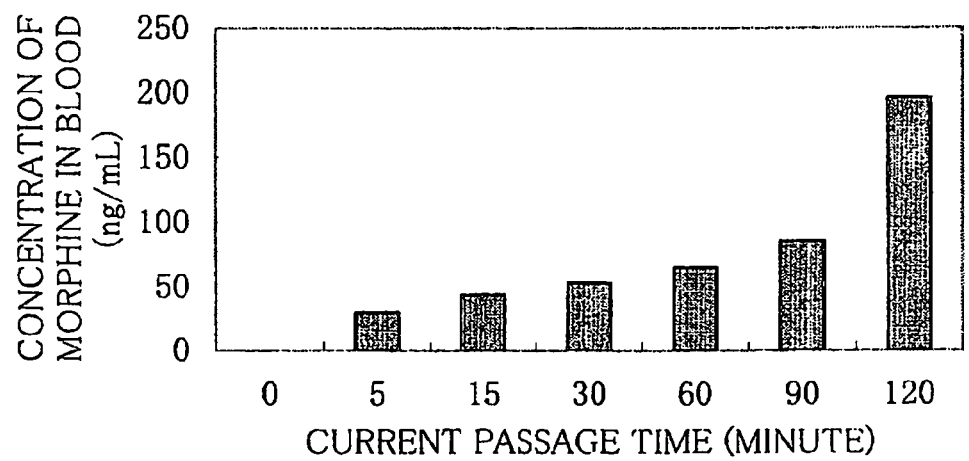
FIG. 4

IONTOPHORESIS DEVICE

BACKGROUND OF THE INVENTION

1. Field of the Invention

The present disclosure relates to an iontophoresis device for administering positively charged drug ions to a living body by an action of a positive electrical potential applied to an active electrode structure holding the drug ions.

2. Description of the Related Art

An iontophoresis device generally includes an active electrode structure holding a drug solution whose active ingredient is dissociated to positive or negative ions (drug ions) and a counter electrode structure that functions as a counter electrode of the active electrode structure. The drug ions are administered to a living body by the application of an electrical potential or voltage with the same polarity as that of the drug ions to the active electrode structure under the condition that both the assemblies are in contact with a biological interface (e.g., skin, mucus membrane) of the living body (e.g., human being or animal).

The charge supplied to the active electrode structure is consumed by the movement of the drug ions to the living body and the release of biological counter ions present in the living body and having a polarity opposite to that of the drug ions) to the active electrode structure. The biological counter ions typically released are those having a small molecular weight (e.g., $Na^+$ and $Cl^-$) and hence high mobility. Therefore, the transport number (i.e., ratio of the amount of current contributing to the movement of the drug ions among the whole current supplied to the active electrode structure) decreases, which makes it difficult or impossible to administer a sufficient amount of drug.

JP 3030517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A and WO 03/037425 disclose iontophoresis devices that attempt to solve the above-mentioned problem.

More specifically, in each of the iontophoresis devices described in the above-cited references, an active electrode structure is composed of an electrode, a drug holding part placed on a front side (i.e., a side facing to the biological interface when in use) of the electrode, and an ion-exchange membrane that is placed on a front side of the drug holding part and selectively passes ions with the same polarity as that of the drug ions held by the drug holding part, and the drug ions are administered through the ion-exchange membrane, whereby the release of biological counter ions is suppressed in an effort to enhance the transport number and thus the administration efficiency of the drug.

In the iontophoresis devices in the above-cited references, the active electrode structure further includes an electrolyte solution holding part for holding an electrolyte solution in contact with the electrode, and an ion-exchange membrane that is placed on a front side of the electrolyte solution holding part that selectively passes ions having a polarity opposite to that of the polarity of the drug ions, and the drug holding part is placed on a front side of the ion-exchange membrane, in an effort to prevent the drug ions from being decomposed, by isolating the drug ions from the electrode and preventing the movement of $H^+$ or $OH^-$ ions generated at the electrode to the drug holding part and the biological interface of a living body.

Furthermore, JP 2004-188188 A discloses a purported improvement over the iontophoresis devices disclosed in JP 3030517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A and WO 03/037425. JP 2004-188188 A teaches that the administration amount of a drug can be enhanced remarkably by using an ion-exchange membrane in which a porous film composed of a material such as polyolefin, vinyl chloride resin, or fluorine resin is filled with an ion-exchange resin (a resin providing an ion-exchange function).

As described above, the iontophoresis device disclosed in JP 2004-188188 A is purported to be the one having the most excellent administration efficiency of a drug among those which are known at present. However, further improvements with respect to administration efficiency of drug delivery are desirable, even as compared with the iontophoresis device disclosed in JP 2004-188188 A.

BRIEF SUMMARY OF THE INVENTION

In one aspect, an iontophoresis device for administering positively charged drug ions includes an active electrode structure having an electrode to which a positive electrical potential or voltage is applied, a drug holding part for holding a drug solution containing drug ions, the drug holding part being placed on a front side of the electrode, and a cellulose-based resin film placed on a front side of the drug holding part.

For example, an iontophoresis device for administering a drug whose active ingredient is dissociated to positive ions in a solution, may employ a cellulose-based resin film in place of the ion-exchanged film placed on a front side of the drug holding part in each of the iontophoresis devices of JP 3030517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A, WO 03/037425 and JP 2004-188188 A.

The cellulose-based resin film functions as a cation exchange membrane. However, the characteristics such as an ion-exchangeability of the cellulose-based resin film are inferior to those of generally used cation exchange membranes (e.g., those illustrated in JP 3030517 B, JP 2000-229128 A, JP 2000-229129 A, JP 2000-237326 A, JP 2000-237327 A, JP 2000-237328 A, JP 2000-237329 A, JP 2000-288097 A, JP 2000-288098 A, WO 03/037425 and JP 2004-188188 A). Accordingly, it has been out of consideration for those skilled in the art to apply the cellulose-based resin film to the iontophoresis device.

In fact, in the study by the inventors of the present subject matter, the characteristics superior to those of the other cation exchange membranes have not been confirmed in vitro evaluation, which is generally performed in an initial stage of development. However, when evaluation was performed in vivo using a living body, it has been found that, according to the above-mentioned iontophoresis device of the present disclosure, the administration efficiency of a drug (i.e., drug administration amount per unit time under the same current conditions from a film surface with the same surface area) is remarkably enhanced, compared with the iontophoresis device using a cation exchange resin disclosed in JP 2004-188188 A.

Herein, examples of the drug whose active ingredient is dissociated to positive ions may include: an anesthetic agent such as morphine hydrochloride or lidocaine; a gastrointestinal disease therapeutic agent such as carnitine chloride; and a skeletal muscle relaxant such as pancuronium bromide.

In another aspect, the drug holding part of the active electrode structure can be configured as a container for holding the above-mentioned drug solution in a liquid state. The drug holding part may hold the drug solution in a gelled or gelatinized form with an appropriate gelling agent. Alternatively, a polymer carrier or the like impregnated with a drug solution may be used as the drug holding part.

The cellulose-based resin film may take the form of a thin film composed of a cellulose-based resin such as regenerated cellulose, cellulose ester, cellulose ether, or cellulose nitrate. Further, a thin film composed of a cellulose-based resin blended or mixed with other components (resin, plasticizer, cross-linker, etc.) can also be used as the cellulose-based resin film, as long as a main component is the cellulose-based resin, and a serious damage to the administration characteristics (administration efficiency, biological compatibility, safety, etc.) of a drug, which impairs the use as an iontophoresis device, is not caused.

Furthermore, the cellulose-based resin film may be a porous film with an appropriate pore size in accordance with the molecular weight of drug ions to be administered. The average pore diameter is typically approximately 1 Å to several μm, and it may be preferable to have a pore size of approximately 1 to 1,000 Å, and or approximately 1 to 100 Å.

In another aspect, the iontophoresis device uses the active electrode structure under the condition that it is attached to the biological interface of a living body. Therefore, it is desired that the cellulose-based resin film used herein have flexibility capable of following the expansion/contraction and bending of the biological interface of the living body and a strength to such a degree not to be broken with a stress caused by such expansion/contraction and bending. Generally, when the thickness of the cellulose-based resin film increases, the strength can be enhanced, while the flexibility is reduced. Therefore, it is preferable that an appropriate thickness be selected in conjunction with the above-mentioned both characteristics in accordance with the kind of the cellulose-based resin film.

In a further aspect, the cellulose-based resin film can incorporate a cation exchange group such as a sulfonic acid group, a carboxylic acid group, or a phosphonic acid group by the action of chlorosulfonic acid, chloracetic acid, an inorganic cyclic triphosphate, or the like. This can further enhance the transport number of drug ions in the administration of a drug, and further enhance the administration efficiency of a drug.

In yet a further aspect, a cellulose-based resin film filled with ion-exchange resin with a cation exchange group introduced thereto can also be used as the cellulose-based resin film. This also may enhance the transport number of drug ions in the administration of a drug, and further increases the administration efficiency of a drug.

Such a cellulose-based resin film can, for example, be obtained by: impregnating a porous thin film body composed of cellulose-based resin with a monomer composition composed of a hydrocarbon type monomer having a function group capable of introducing a cation exchange group, a cross-linkable monomer, and a polymerization initiator; and allowing chlorosulfonic acid, chloracetic acid, an inorganic cyclic triphosphate, etc. to act on the resultant porous thin film body.

A sulfonic acid group that is a strong acid group is may be preferable as the cation exchange group to be introduced to the above-mentioned cellulose-based resin film or ion-exchange resin.

Furthermore, each of the above cation exchange groups may be present as a free acid, or may be present as a salt with alkaline metal ions such as sodium ions and potassium ions, ammonium ions, etc.

In still another aspect, an iontophoresis device may comprise an active electrode structure having: an electrode to which a positive electrical potential or voltage is applied; a drug holding part for holding a drug solution containing positively charged drug ions, the drug holding part being placed on a front side of the electrode; and a complex film composed of a cation exchange membrane and a cellulose-based resin film placed on a front side of the cation exchange membrane, the complex film being placed on a front side of the drug holding part, in which the drug ions are administered through the cellulose-based resin film. This may further enhance the transport number in the administration of a drug, and further enhance the administration efficiency of a drug.

The complex film as mentioned above can also be used as the cellulose-based resin film of the previously described embodiments.

In this case, it may be preferable to use as the cation exchange membrane a configuration filled with an ion-exchange resin in which a cation exchange group is introduced to a porous film made of a material such as polyolefin, a vinyl chloride resin, or a fluorine resin. This may further enhance the transport number in the administration of a drug.

In the above-mentioned complex film, in order to prevent an air layer from being present at an interface between the cation exchange membrane and the cellulose-based resin film, it may be preferable to bond the interface between them so as to integrate the cation exchange membrane and the cellulose-based resin film.

Examples of a bonding method include adhesion by heat sealing, ultrasonic bonding, adhesion with an adhesive such as a cyanoacrylate-type adhesive, and a cross-linking reaction with a cross-linker such as divinylbenzene. Alternatively, a cellulose-based resin film is formed on a cation exchange membrane (e.g., cellulose is regenerated by allowing sulfuric acid to act on a cellulose copper ammonia solution applied to a cation exchange membrane), whereby the cation exchange membrane can be bonded to the cellulose-based resin film.

Herein, in the case of bonding the cation exchange membrane to the cellulose-based resin film by the adhesion, cross-linking reaction, or formation of a cellulose-based resin film on a cation exchange membrane, it may be preferable to perform bonding under the condition that at least the surface of a cation exchange membrane facing the cellulose-based resin film is roughened by an approach such as embossing, grooving, notching, mechanical polishing, or chemical polishing. This may enhance the adhesion and integration of the cation exchange membrane and the cellulose-based resin film.

Furthermore, the cation exchange membrane can also be roughened by mixing an inorganic filler such as calcium carbonate or magnesium carbonate, or an organic filler such as denatured polyethylene particles or denatured polyacrylic acid resin particles, with a resin film constituting the cation exchange membrane.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

In the accompanying drawings:

FIG. 3A is a graph showing a time transition of the concentration of morphine in the blood before and after the administration of a drug, when morphine hydrochloride is administered to a mouse using the iontophoresis device according to one illustrated embodiment.

FIG. 3B is a chart showing a pH value (b) of a drug solution and an electrolyte solution before and after the administration of a drug, when morphine hydrochloride is administered to a mouse using the iontophoresis device according to one illustrated embodiment.

FIG. 4 is a graph showing a time transition of the concentration of morphine in the blood, when morphine hydrochloride is administered to a mouse using a conventional iontophoresis device.

DESCRIPTION OF THE PREFERRED EMBODIMENTS

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with iontophoresis devices, ion exchange membranes, power sources, voltage and/or current regulators and controllers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
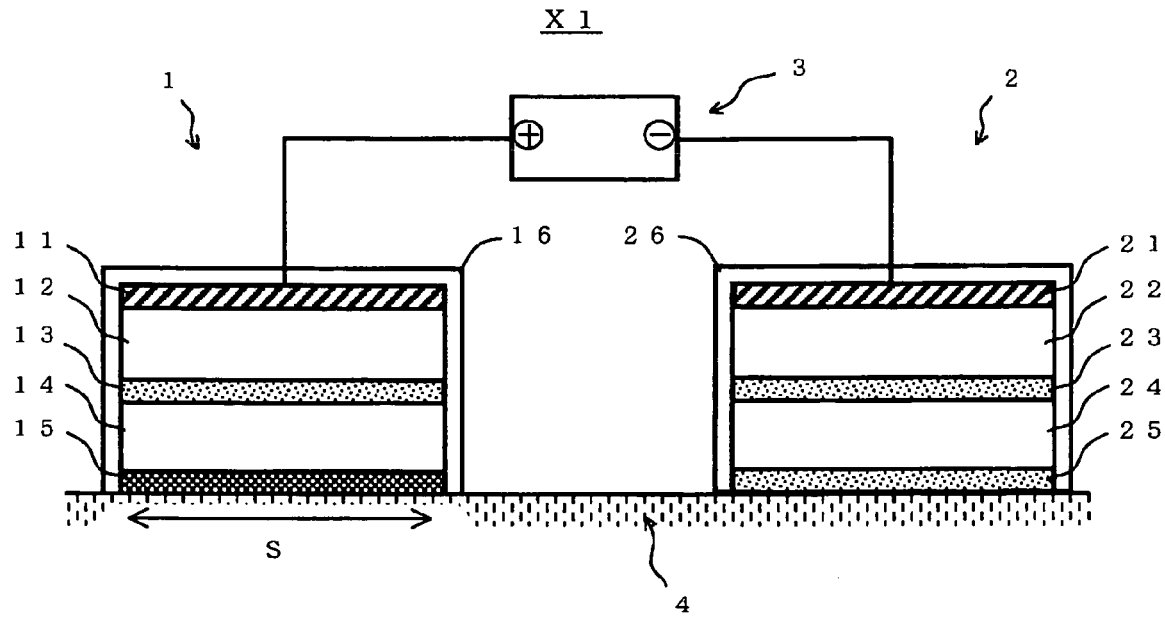
FIG. 1 is a schematic diagram showing a configuration of an iontophoresis device according to one illustrated embodiment.

FIG. 1 shows an iontophoresis device X1, including an active electrode structure 1, a counter electrode structure 2, and a power source 3, as main components (members). Reference numeral 4 denotes a biological interface such as skin or a mucous membrane.

The active electrode structure 1 includes an electrode 11 electrically coupleable to a positive pole of the power source 3, an electrolyte solution holding part 12 for holding an electrolyte solution in contact with or proximate the electrode 11, an anion exchange membrane 13 placed on a front side of the electrolyte solution holding part 12, a drug holding part 14 placed on a front side of the anion exchange membrane 13, and a cellulose-based resin film 15 placed on a front side of the drug holding part 14. The entire active electrode structure 1 is housed in a cover or a container 16 composed of a material, for example, a resin film or a plastic.

On the other hand, the counter electrode structure 2 includes an electrode 21 connected to a negative pole of the power source 3, an electrolyte solution holding part 22 for holding an electrolyte solution in contact with or proximate the electrode 21, a cation exchange membrane 23 placed on a front side of the electrolyte solution holding part 22, an electrolyte solution holding part 24 placed on a front side of the cation exchange membrane 23, and an anion exchange membrane 25 placed on a front side of the electrolyte solution holding part 24. The entire counter electrode structure 2 is housed in a cover or a container 26 composed of a material, for example, a resin film or a plastic.

In the iontophoresis device X1, those which are made of any conductive material can be used as the electrodes 11 and 21 without any particular limit. In particular, a counter electrode composed of carbon, platinum, or the like may be preferred, and a carbon electrode free from the elution of metal ions and the transfer thereof to a living body may be more preferred.

However, an active electrode such as a silver/silver chloride couple electrode in which the electrode 11 is made of silver and the electrode 21 is made of silver chloride can also be adopted.

For example, in the case of using the silver/silver chloride couple electrode, in the electrode 11 that is a positive pole, a silver electrode and chlorine ions ($Cl^-$) easily react with each other to generate insoluble AgCl as represented by $Ag^+Cl^- \rightarrow AgCl+e^-$, and in the electrode 21 that is a negative pole, chlorine ions ($Cl^-$) are eluted from a silver chloride electrode. Consequently, the following effects may be obtained: the electrolysis of water is suppressed, and the rapid acidification based on $H^+$ ions at the positive pole, and the rapid basification based on $OH^-$ ions at the negative pole can be prevented.

In contrast, in the active electrode structure 1 and the counter electrode structure 2 in the iontophoresis device X1 in FIG. 1, owing to the function of the anion exchange membrane 13 and the cation exchange membrane 23, the rapid acidification based on $H^+$ ions in the electrolyte solution holding part 12 and the rapid basification based on $OH^-$ ions in the electrolyte solution holding part 22 may be suppressed. Therefore, an inexpensive carbon electrode free from the elution of metal ions can be advantageously used in place of the active electrode such as a silver/silver chloride couple electrode.

Furthermore, the electrolyte solution holding parts 12, 22, and 24 in the iontophoresis device X1 in FIG. 1 hold an electrolyte solution so as to maintain the conductivity. Phosphate buffered saline, physiological saline, etc. can be used as the electrolyte solution typically.

Furthermore, in order to more effectively prevent the generation of gas caused by the electrolytic reaction of water and the increase in a conductive resistance caused by the generation of gas, or the change in pH caused by the electrolytic reaction of water, an electrolyte that is more readily oxidized or reduced (i.e., oxidation at the positive pole and the reduction at the negative pole) than the electrolytic reaction of water can be added to the electrolyte solution holding parts 12 and 22. In terms of the biological safety and economic efficiency (e.g., low cost and easy availability), for example, an inorganic compound such as ferrous sulfate or ferric sulfate, a medical agent such as ascorbic acid (vitamin C) or sodium ascorbate, and an organic acid such as lactic acid, oxalic acid, malic acid, succinic acid, or fumaric acid and/or a salt thereof may be preferred. Alternatively, a combination of those substances (for example, 1:1 mixed aqueous solution containing 1 mol (M) of lactic acid and 1 mol (M) of sodium fumarate) can also be used.

The electrolyte solution holding parts 12, 22, and 24 may hold the above-mentioned electrolyte solution in a liquid state. However, the electrolyte solution holding parts 12, 22, and 24 may be configured by impregnating a water-absorbing thin film carrier made of a polymer material or the like with the above-mentioned electrolyte solution, thereby enhancing the ease of handling thereof. The same thin film carrier as that can be used in the drug holding part 14 can be used as the thin film carrier described herein. Therefore, the detail thereof will be described in the following description regarding the drug holding part 14.

The drug holding part 14 in the iontophoresis device X1 according to this embodiment holds at least an aqueous solution of a drug whose active ingredient is dissociated to positive drug ions by the dissolution, as a drug solution.

Herein, the drug holding part 14 may hold a drug solution in a liquid state. However, it is also possible to impregnate such a water-absorbing thin film carrier as described below with a drug solution so as to enhance the ease of handling thereof.

Examples of a material that can be used for the water-absorbing thin film carrier in this case include a hydrogel body of acrylic resin (acrylhydrogel film), segmented polyurethane gel film, and/or an ion conductive porous sheet for forming a gel solid electrolyte. By impregnating the above aqueous solution at an impregnation ratio of 20 to 60%, a high transport number (high drug delivery property), e.g., 70 to 80% may be obtained.

The impregnation ratio in the present specification is represented by % by weight (i.e., $100 \times (W-D)/D[\%]$ where D is a weight in a dry state and W is a weight after impregnation). The impregnation ratio should be measured immediately after the impregnation with an aqueous solution to eliminate a chronological influence.

Furthermore, the transport number refers to the ratio of the amount of current contributing to the transfer of particular ions among the whole current flowing through the electrolyte solution. In the present specification, the transport number is used in terms of that regarding drug ions, i.e., the ratio of a current contributing to the transfer of drug ions among the whole currents supplied to the active electrode structure.

Herein, the above-mentioned acrylhydrogel film (for example, available from Sun Contact Lens Co., Ltd.) is a gel body having a three-dimensional network structure (i.e., cross-linking structure). When an electrolyte solution that is a dispersion medium is added to the acrylhydrogel film, the acrylhydrogel film becomes a polymer adsorbent having ion conductivity. Furthermore, the relationship between the impregnation ratio of the acrylhydrogel film and the transport number can be adjusted by controlling the size of the three-dimensional network structure and the kind and ratio of a monomer constituting a resin. The acrylhydrogel film with an impregnation ratio of 30 to 40% and a transport number of 70 to 80% can be prepared from 2-hydroxyethylmethacrylate and ethyleneglycol dimethacrylate (monomer ratio 98 to 99.5: 0.5 to 2), and it is confirmed that the impregnation ratio and transport number are almost the same in a range of an ordinary thickness of 0.1 to 1 mm.

Furthermore, the segmented polyurethane gel film has, as segments, polyethylene glycol (PEG) and polypropylene glycol (PPG), and can be synthesized from a monomer and diisocyanate constituting these segments. The segmented polyurethane gel film has a three-dimensional structure crosslinked by a urethane bond, and the impregnation ratio, transport number, and adhesion strength of the gel film can be easily adjusted by controlling the size of a network, and the kind and ratio of a monomer in the same way as in the acrylhydrogel film. When water that is a dispersion medium and an electrolyte (alkaline metal salt, etc.) are added to the segmented polyurethane gel film (porous gel film), oxygen in an ether connecting part of polyether forming a segment and an alkaline metal salt form a complex, and ions of the metal salt move to oxygen in a subsequent blank ether connecting part when a current flows, whereby the conductivity is expressed.

As the ion conductive porous sheet for forming a gel solid electrolyte, for example, there is the one disclosed in JP 11-273452 A. This porous sheet is based on an acrylonitrile copolymer, and a porous polymer with a porosity of 20 to 80%. More specifically, this porous sheet is based on an acrylonitrile copolymer with a porosity of 20 to 80% containing 50 mol % or more (preferably 70 to 98 mol %) of acrylonitrile. The acrylonitrile gel solid electrolytic sheet (solid-state battery) is prepared by impregnating an acrylonitrile copolymer sheet soluble in a non-aqueous solvent and having a porosity of 20 to 80%, with a non-aqueous solvent containing an electrolyte, followed by gelling, and a gel body includes a gel to a hard film.

In terms of the ion conductivity, safety, and the like, it may be preferable to compose the acrylonitrile copolymer sheet soluble in a non-aqueous solvent of an acrylonitrile/C1 to C4 alkyl (meth)acrylate copolymer, an acrylonitrile/vinylacetate copolymer, an acrylonitrile/styrene copolymer, an acrylonitrile/vinylidene chloride copolymer, or the like. The copolymer sheet is made porous by an ordinary method such as a wet (dry) paper making method, a needlepunching method that is a kind of a non-woven fabric producing method, a water-jet method, drawing perforation of a melt-extruded sheet, or perforation by solvent extraction. Among the above-mentioned ion conductive porous sheets of an acrylonitrile copolymer used in a solid-state battery, a gel body (a gel to a hard film) holding the above-mentioned aqueous solution in a three-dimensional network of a polymer chain and in which the above-mentioned impregnation ratio and transport number are achieved is useful as a thin film carrier used in the drug holding part 14 or the electrolyte solution holding parts 12, 22, and 24.

Regarding the conditions for impregnating the above-mentioned thin film carrier with a drug solution or an electrolyte solution, the optimum conditions may be determined in terms of the impregnation amount, impregnation speed, and the like. For example, an impregnation condition of 30 minutes at 40° C. may be selected.

An ion-exchange membrane carrying an ion-exchange resin having an anion exchange function in a base, for example, NEOSEPTA, AM-1, AM-3, AMX, AHA, ACH, ACS, ALE04-2, AIP-21, produced by Tokuyama Co., Ltd. can be used as the anion exchange membrane (ion-exchange membrane having characteristics of selectively passing negative ions) 13 and 25 in the iontophoresis device X1 according to this embodiment. An ion-exchange membrane carrying an ion-exchange resin having a cation exchange function in a base, for example, NEOSEPTA, CM-1, CM-2, CMX, CMS, CMB, CLE04-2, produced by Tokuyama Co., Ltd. can be used as the cation exchange membrane (ion-exchange membrane having characteristics of selectively passing positive ions) 23. In particular, a cation exchange membrane in which a part or an entirety of a pore of a porous film is filled with an ion-exchange resin having a cation exchange function, or an anion exchange membrane filled with an ion-exchange resin having an anion exchange function can be used preferably.

Herein, a fluorine type resin with an ion-exchange group introduced to a perfluorocarbon skeleton or a hydrocarbon type resin containing a resin that is not fluorinated as a skeleton can be used as the above-mentioned ion-exchange resin. In view of the convenience of a production process, a hydrocarbon type ion-exchange resin is preferable. Furthermore, although the filling ratio of the ion-exchange resin is also related to the porosity of the porous film, the filling ratio is generally 5 to 95% by mass, in particular, approximately 10 to 90% by mass, and may be preferred to be approximately 20 to 60% by mass.

Furthermore, there is no particular limit to an ion-exchange group of the above-mentioned ion-exchange resin, as long as it is a functional group generating a group having negative or positive charge in an aqueous solution. As specific examples of the functional group to be such an ion-exchange group, those of a cation exchange group include a sulfonic acid group, a carboxylic acid group, and a phosphonic acid group. Those acid groups may be present in the form of a free acid or a salt. Examples of a counter cation in the case of a salt include alkaline metal cations such as sodium ions and potassium ions, and ammonium ions. Of those cation exchange groups, generally, a sulfonic acid group that is a strong acidic group is particularly preferable. Furthermore, examples of the anion exchange group include primary to tertiary amino groups, a quaternary ammonium group, a pyridyl group, an imidazole group, a quaternary pyridinium group, and a quaternary imidazolium group. Examples of a counter anion in those anion exchange groups include halogen ions such as chlorine ions and hydroxy ions. Of those anion exchange groups, generally, a quaternary ammonium group and a quaternary pyridinium group that are strong basic groups are used preferably.

Furthermore, a film shape or a sheet shape having a number of small holes passing from front to back sides are used as the above-mentioned porous film without any particular limit. In order to satisfy both the high strength and the flexibility, the porous film may be made of a thermoplastic resin.

Examples of the thermoplastic resins constituting the porous film include, without limitation: polyolefin resins such as homopolymers or copolymers of α-olefins such as ethylene, propylene, 1-butene, 1-pentene, 1-hexene, 3-methyl-1-butene, 4-methyl-1-pentene, and 5-methyl-1-heptene; vinyl chloride resins such as polyvinyl chloride, vinyl chloride-vinyl acetate copolymers, vinyl chloride-vinylidene chloride copolymers, and vinyl chloride-olefin copolymers; fluorine resins such as polytetrafluoroethylene, polychlorotrifluoroethylene, polyvinylidene fluoride, tetrafluoroethylene-hexafluoropropylene copolymers, tetrafluoroethylene-perfluoroalkyl vinylether copolymers, and tetrafluoroethylene-ethylene copolymers; polyamide resins such as nylon 6 and nylon 66; and those which are made from polyamide resins. Polyolefin resins may be preferable as they are superior in mechanical strength, flexibility, chemical stability, and chemical resistance, and have good compatibility with ion-exchange resins. As the polyolefin resins, polyethylene and polypropylene may be particularly preferable and polyethylene may be most preferable.

There is no particular limit to the property of the above-mentioned porous film made of the thermoplastic resin. However, the average pore diameter of pores of approximately 0.005 to 5.0 μm may be preferred, while approximately 0.01 to 2.0 μm may be more preferred, and approximately 0.02 to 0.2 μm may be most preferred since the porous film having such an average pore diameter is likely to be a thin ion-exchange membrane having excellent strength and a low electric resistance. The average pore diameter in the present specification refers to an average flow pore diameter measured in accordance with a bubble point method (JIS K3832-1990). Similarly, the porosity of the porous film of approximately 20 to 95% may be preferred, while approximately 30 to 90% may be more preferred, and approximately 30 to 60% may be most preferred. Furthermore, the thickness of the porous film may of approximately 5 to 140 μm, approximately 10 to 120 μm may be even more preferred, and approximately 15 to 55 μm may be most preferred. Usually, an anion exchange membrane or a cation exchange membrane using such a porous film has a thickness of the porous film with +0 to 20 μm.

The cellulose-based resin film 15 used in the iontophoresis device X1 according to this embodiment can be constituted by cellulose-based resins such as regenerated cellulose manufactured by a method such as a cuprammonium process or a tertiary amineoxide process, cellulose esters (e.g., cellulose acetate, cellulose propionate, or cellulose acetate butyrate), cellulose ethers (e.g., hydroxyethyl cellulose or hydroxypropyl cellulose) or nitrocellulose. A porous thin film of cellulose-based resins having an average pore diameter of approximately 1 Å to a few μm may be preferred, approximately 1 to 1,000 Å may be more preferred, and around 1 to 100 Å may be particularly preferred, and a thickness of approximately 10 to 200 μm may be preferred, and approximately 20 to 50 μm may be particularly preferred.

A cation exchange group such as a sulfonic acid group, a carboxylic acid group, or a phosphonic acid group can be introduced to the above-mentioned cellulose-based resin film by allowing chlorosulfonic acid, chloroacetic acid, inorganic cyclic triphosphate, or the like to act on the cellulose-based resin film. By using a cellulose-based resin film with such a cation exchange group introduced thereto as the cellulose-based resin film 15, the administration efficiency of a drug can be enhanced further.

Alternatively, a porous thin film made of the above-mentioned cellulose-based resin in which pores are filled with a cation exchange resin can also be used for the cellulose-based resin film 15.

The cellulose-based resin film filled with a cation exchange resin can be obtained by: impregnating the above-mentioned porous thin film made of a cellulose-based resin with a monomer composition composed of a hydrocarbon type monomer having a functional group capable of introducing a cation exchange group, a cross-linkable monomer, and a polymerization initiator; polymerizing them under appropriate reaction conditions; and allowing chlorosulfonic acid, chloracetic acid, an inorganic cyclic triphosphate, or the like to act on the resultant porous thin film.

Examples of the hydrocarbon-type monomer having a functional group capable of introducing a cation exchange group include aromatic vinyl compounds such as styrene, α-methylstyrene, 3-methylstyrene, 4-methylstyrene, 2,4-dimethylstyrene, p-tert-butylstyrene, α-halogenated styrene, and vinylnaphthalene and each one or more of them can be used. Examples of an available cross-linkable monomer include: polyfunctional vinyl compounds such as divinylbenzenes, divinyl sulfone, butadiene, chloroprene, divinylbiphenyl, and trivinylbenzene; and polyfunctional methacrylic acid derivatives such as trimethylol methane trimethacrylate, methylenebis acrylamide, and hexamethylene methacrylamide. Examples of an available polymerization initiator include octanoyl peroxide, lauroyl peroxide, t-butylperoxy-2-ethylhexanoate, benzoyl peroxide, t-butyl peroxyisobutyrate, t-butyl peroxylaurate, t-hexyl peroxybenzoate, and di-t-butylperoxide.

In addition to the above components, other hydrocarbon-type monomers which are copolymerizable with the above hydrocarbon-type monomers and cross-linkable monomers, or plasticizers may be added as required. Examples of the other monomers which may be used include acrylonitrile, acrolein, and methylvinylketone. Further, examples of the plasticizers which may be used include dibutyl phthalate, dioctyl phthalate, dimethyl isophthalate, dibutyladipate, triethylcitrate, acetyltributylcitrate, dibutylsebacate, and dibenzylether.

A battery, a voltage stabilizer, a current stabilizer (galvano device), a voltage/current stabilizer, or the like can be used as the power source 3 in the iontophoresis device. It may be preferable to use a current stabilizer that is operated under safe voltage conditions in which an arbitrary current can be adjusted in a range of approximately 0.01 to 1.0 mA, while approximately 0.01 to 0.5 mA, specifically, at approximately 50V or less may be preferred and approximately 30 V or less may be even more preferred.

The iontophoresis device X1 according to this embodiment has remarkably higher administration efficiency of a drug than that of a conventional iontophoresis device using a cation exchange membrane in place of the cellulose-based resin film 15, as described later in examples.

Figure 2:
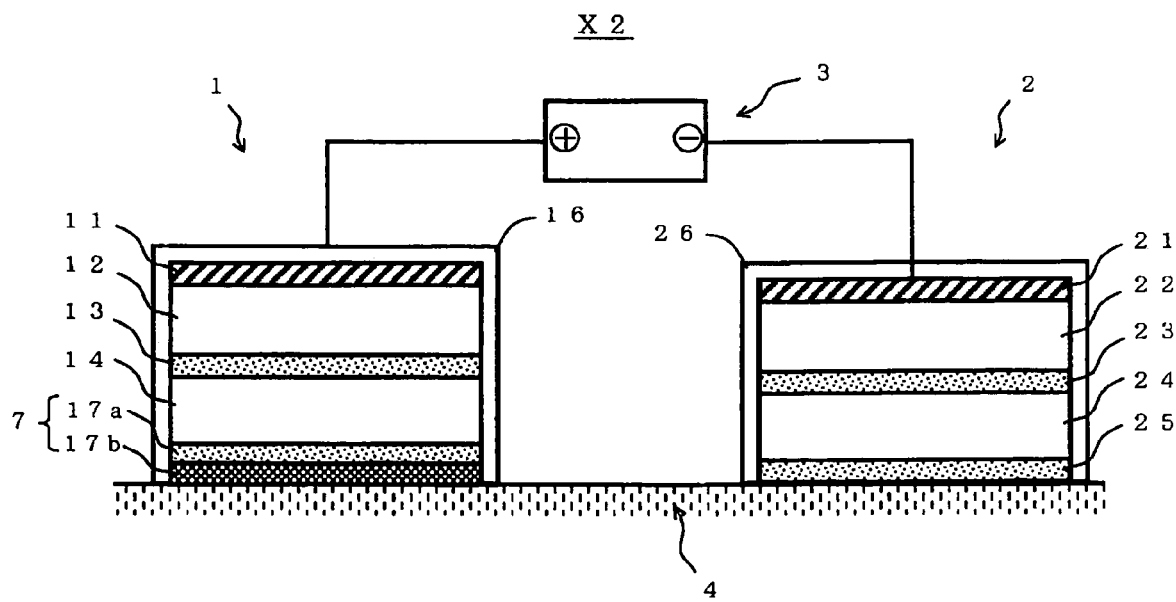
FIG. 2 is a schematic diagram showing a configuration of an iontophoresis device according to another illustrated embodiment.

FIG. 2 illustrates a configuration of an iontophoresis device X2 according to another embodiment.

As shown in FIG. 2, the iontophoresis device X2 has the same configuration as that of the above-mentioned iontophoresis device X1, except that a complex film 17 made of a cation exchange membrane 17a placed on a front side of the drug holding part 14 and a cellulose-based resin film 17b placed on a front side of the cation exchange membrane 17a is provided, in place of the cellulose-based resin film 15.

The same cation exchange membrane as that described with respect to the cation exchange membrane 23 can be used as the cation exchange membrane 17a of the complex film 17. The same cellulose-based resin film as that described with respect to the cellulose-based resin film 15 can be used as the cellulose-based resin film 17b.

In order to prevent an air layer from being present at an interface between the cation exchange membrane 17a and the cellulose-based resin film 17b, it may be preferable that the complex film 17 be formed by bonding the interface between the cation exchange membrane 17a and the cellulose-based resin film 17b by heat sealing, ultrasonic bonding, adhesion with an adhesive, chemical bonding with a cross-linker, or formation of the cellulose-based resin film 17b on the cation exchange membrane 17a. In the case of bonding by means of the adhesion, chemical bonding, or the like, in order to make the integration and adhesion of the bonding satisfactory, it may be preferable to use the cellulose-based resin film 17b in which at least the connection side surface is roughened by an approach such as embossing, grooving, notching, mechanical polishing, or chemical polishing, or by mixing an inorganic filler such as calcium carbonate or magnesium carbonate and an organic filler such as denatured polyethylene particles or denatured polyacrylic acid resin particles with a cellulose-based resin.

The condition of heat sealing and ultrasonic bonding, the kind and adhesion condition of an adhesive, the kind and cross-linking condition of a cross-linker, and the like can be appropriately determined depending upon the kind of the cation exchange membrane 17a (mainly, the kind of a porous resin film used in the cation exchange membrane 17a) and the kind of the cellulose-based resin film 17b. The connection herein may prevent the administration efficiency of a drug from decreasing due to the presence of an air layer at the interface between the cation exchange membrane 17a and the cellulose-based resin film 17b. Therefore, the bonding should be sufficiently strong such that the interface will not be peeled off due to the expansion/contraction and bending of the skin while the iontophoresis device is mounted.

In the iontophoresis device X2 according to this embodiment, the ion-exchange ability of the complex film 17 is enhanced by the cation exchange membrane 17a, so that the transport number in the administration of a drug can be increased, and the administration efficiency of a drug comparable to or higher than that of the iontophoresis device X1 can be obtained.

EXAMPLE 1 (IN VIVO TEST 1)

Using a C57BL/6 mouse (male) of 20 to 24 weekly age as a test animal, an administration test of morphine hydrochloride in the above-mentioned iontophoresis device X1 was performed.

NEOSEPTA ALE04-2 produced by Tokuyama Co., Ltd. was used as each of the anion exchange membranes 13 and 25 of the iontophoresis device X1. NEOSEPTA CLE04-02 produced by Tokuyama Co., Ltd. was used as the cation exchange membrane 23. A regenerated cellulose dialysis membrane UC8-32-25 (average pore diameter: 50 Å, transmission molecular weight (MWCO): about 14,000, film thickness: 50 μm) of 99% α-cellulose obtained from Viskase Sales Co. (Illinois in the US) was used as the cellulose-based resin film 15. 50 mg/mL of morphine hydrochloride was used as a drug solution of the drug holding part 14. A 7:1 mixed solution of 0.7 mol/L sodium fumarate aqueous solution and 0.7 mol/L lactic acid aqueous solution was used as an electrolyte solution of the electrolyte solution holding parts 12, 22, and 24. The effective area of the active electrode structure 1 (area of a film surface of the cellulose-based resin film 15 through which a drug is administered (see the reference S in FIG. 1) was 2.23 $cm^2$.

The drug was administered under the condition that the active electrode structure 1 and the counter electrode structure 2 were brought into contact with different sites of the shaved abdomen of the mouse, and a constant current was allowed to flow continuously at 0.45 mA/$cm^2$ for 120 minutes.

FIG. 3A shows the transition of the concentration of morphine in the blood of the mouse during the passage of a current under the above-mentioned conditions, and FIG. 3B shows the pH values of the electrolyte solution of the electrolyte solution holding parts 12, 22, and 24, and the drug solution of the drug holding part 14 before the commencement of the passage of a current and after the completion thereof.

COMPARATIVE EXAMPLE 1 (IN VIVO TEST 2)

Using an iontophoresis device with the same configuration as that of the iontophoresis device X1 of Example 1 except for using a cation exchange membrane (NEOSEPTA CLE04-2 produced by Tokuyama Co., Ltd.) in place of the cellulose-based resin film 15, morphine hydrochloride was administered to the mouse under the same conditions as those of Example 1.

Here, NEOSEPTA ALE04-2 that is an anion exchange membrane and CLE04-2 that is a cation exchange membrane are ion-exchange membranes each having a configuration in which a pore of a porous film is filled with an ion-exchange resin. Therefore the iontophoresis device used in Comparative Example 1 has the same configuration as that of the iontophoresis device of JP 2004-188188 A that is considered to exhibit the highest administration efficiency of a drug in the prior art.

FIG. 4 shows the transition of the concentration of morphine in the blood of the mouse during the passage of a current in Comparative Example 1.

REFERENCE EXAMPLE 1 (IN VITRO TEST 1)

A test device having a configuration equivalent to that of the iontophoresis device X1 used in Example 1 was produced, and a constant current was allowed to flow continuously at 0.45 mA/cm$^2$ for 120 minutes.

Figure 5:
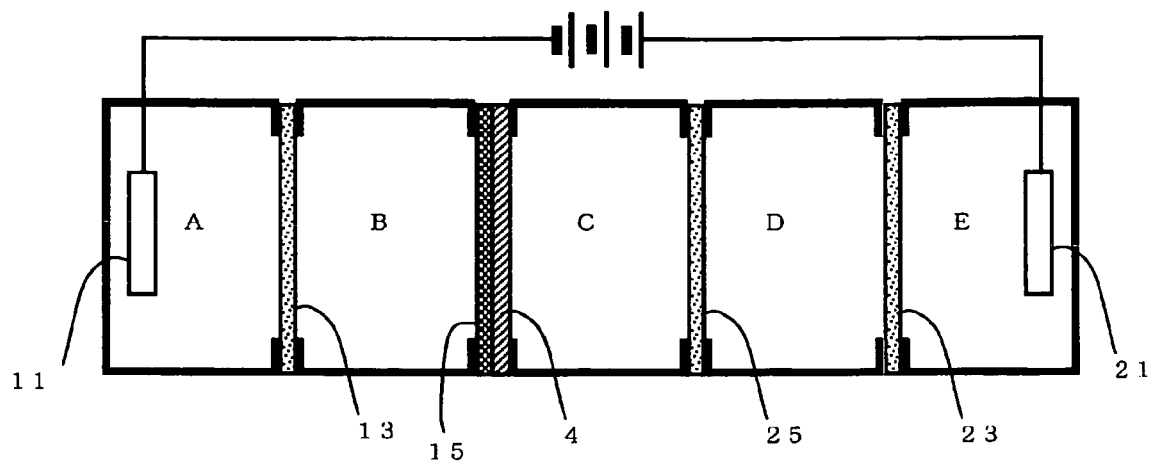
FIG. 5 is a schematic diagram showing a configuration of a test device used for evaluating morphine transfer characteristics in vitro.

FIG. 5 illustrates the configuration of the test device. In FIG. 5, Reference numerals 11 and 21 denote electrodes. Reference numerals 13 and 25 denote anion exchange membranes (i.e., NEOSEPTA ALE04-2 produced by Tokuyama Co., Ltd.). Reference numeral 23 denotes a cation exchange membrane (i.e., NEOSEPTA CLE04-2 produced by Tokuyama Co., Ltd.). Reference numeral 15 denotes a cellulose-based resin film (i.e., dialysis membrane UC8-32-25 produced by Viskase Sales Co.). Reference numeral 4 denotes the skin collected from a mouse. An A-chamber, a D-chamber and an E-chamber are filled with a mixed solution (7:1) of 0.7 mol/L sodium fumarate aqueous solution and 0.7 mol/L lactic acid aqueous solution as an electrolyte solution. A B-chamber is filled with 50 mg/mL of morphine hydrochloride as a drug solution. A C-chamber is filled with physiological saline.

Figure 6:
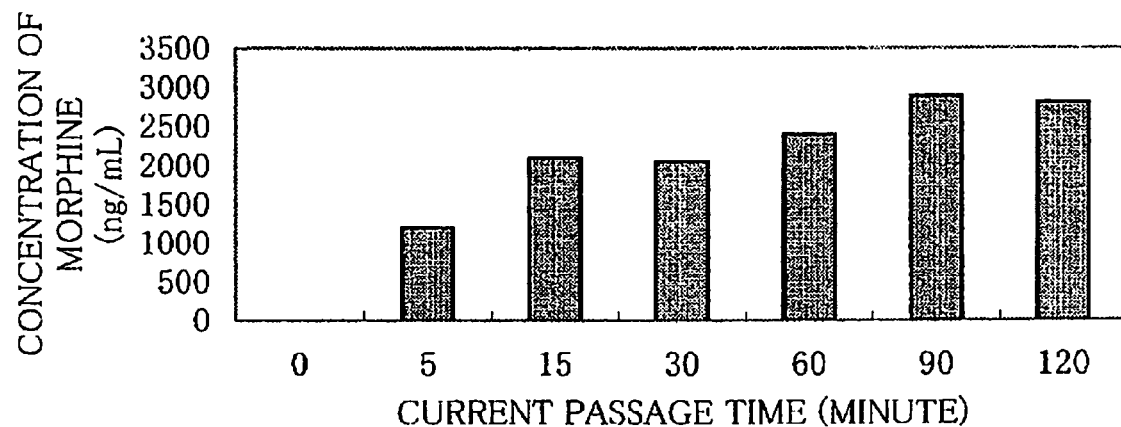
FIG. 6 is a graph showing evaluation results of morphine transfer characteristics in a test device equivalent to the iontophoresis device disclosed herein.

FIG. 6 shows the transition of the concentration of morphine in the C-chamber during the passage of a current in Reference Example 1.

COMPARATIVE REFERENCE EXAMPLE 1 (IN VITRO TEST 2)

Using the same test device as that of Reference Example 1 except for using a cation exchange membrane (i.e., NEOSEPTA CLE04-2 produced by Tokuyama Co., Ltd.) in place of the cellulose-based resin film 15 in FIG. 5, which has an equivalent configuration to the iontophoresis device used in Comparative Example 1, a constant current was allowed to flow continuously at 0.45 mA/cm$^2$ for 120 minutes.

Figure 7:
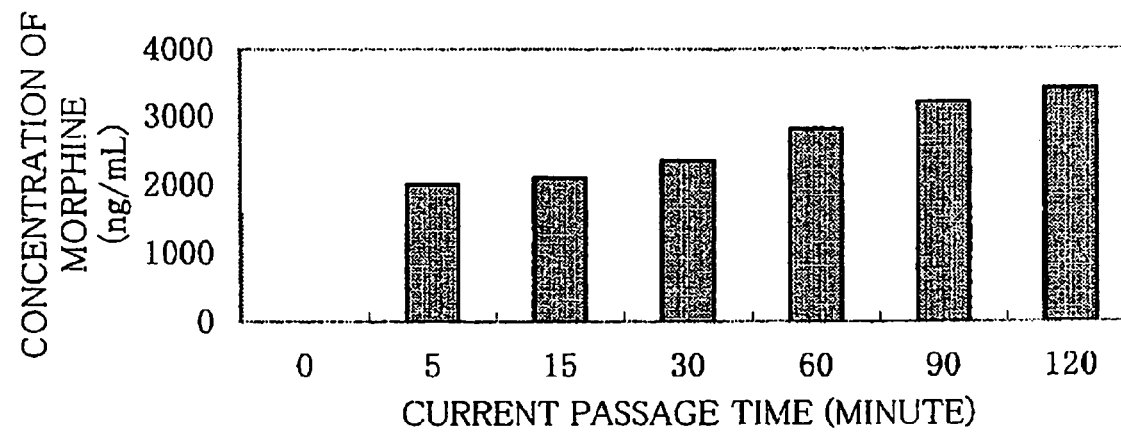
FIG. 7 is a graph showing evaluation results of morphine transfer characteristics in a test device equivalent to a conventional iontophoresis device.

FIG. 7 shows the transition of the concentration of morphine in the C-chamber during the passage of a current in Comparative Reference Example 1.

As is apparent from the comparison between FIG. 3A and FIG. 4, the iontophoresis device, employing the cellulose-based resin film 15, may administer morphine at efficiency of approximately 5 to 10 times or more, even as compared with the iontophoresis device having the configuration of Comparative Example 1 in which the administration efficiency of a drug has been conventionally considered to be highest.

Furthermore, as shown in FIG. 3B, in the electrolyte solution in the electrolyte solution holding parts 12, 22, and 24 and the drug solution of the drug holding part 14 of the iontophoresis device, employing the cellulose-based resin film 15, the pH values hardly changed before and after the passage of a current. Thus, it is understood that the biological compatibility, safety and stability of the administration of a drug may be ensured.

Furthermore, as shown in FIGS. 6 and 7, in the in vitro test, the transfer speed of morphine in the test device (Reference Example 1) with the cellulose-based resin film 15 was inferior by about tens of percentages to that of the test device (Comparative Reference Example 1) with the conventional configuration.

In the technical field of iontophoresis, the evaluation and study in vitro are generally performed without using a living body in a stage of selecting the material of a member of a device and the like. As described above, the effect of using a cellulose-based resin film can only be confirmed by the evaluation in vivo, and can not be confirmed by the evaluation in vitro, and this fact is considered to be a proof of the difficulty in constituting the present invention.

The present invention has been described with reference to the illustrated embodiments. The present invention is not limited thereto, and various alterations can be made within the scope of the claims.

For example, in the above embodiment, the case has been described where the active electrode structure includes the electrolyte solution holding part 12 and the anion exchange membrane 13, in addition to the electrode 11, the drug holding part 14, and the cellulose-based resin film 15 (or the complex film 17). However, the electrolyte solution holding part 12 and the ion-exchange membrane 13 can also be omitted. In this case, although the function of suppressing the decomposition of a drug in the vicinity of the electrode 11, the movement of H$^+$ ions to the skin interface, the function of suppressing the variation in pH at the skin interface caused by the movement of H$^+$ ions, and the like cannot be achieved to such a degree as that in the above-mentioned embodiment, the administration efficiency of a drug to a living body may be achieved similarly, and such an iontophoresis device is also included in the scope of the present invention.

Similarly, regarding the counter electrode structure, the cation exchange membrane 23 and the electrolyte solution holding part 24, or the anion exchange membrane 25 in addition to the cation exchange membrane 23 and the electrolyte solution holding part 24 can be omitted. In this case, although the performance of suppressing the change in pH in a contact surface of the counter electrode structure 2 with respect to the skin 4 cannot be achieved to such a degree as that in the above-mentioned embodiment, the administration efficiency of a drug to a living body may be achieved similarly, and such an iontophoresis device is also included in the scope of the present invention.

Alternatively, it is also possible that the counter electrode structure 2 is not provided in the iontophoresis device, and for example, under the condition that the active electrode structure is brought into contact with the biological interface of a living body and a part of the living body is brought into contact with a ground such as an electrical coupling to earth, a drug is administered by applying an electrical potential or voltage to the active electrode structure. Such an iontophoresis device may also similarly enhance the administration efficiency of a drug to a living body and is included in the scope of the present invention.

Furthermore, in the above embodiment, the case has been described where the active electrode structure, the counter electrode structure, and the power source are configured separately. It is also possible that those elements are incorporated in a single casing or an entire device incorporating them is formed in a sheet shape or a patch shape, whereby the handling thereof is enhanced, and such an iontophoresis device is also included in the scope of the present invention.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An iontophoresis device, comprising an active electrode structure comprising:
   an electrode to which a positive electrical potential is applied;
   a drug holding part for holding a drug solution containing positively charged drug ions, the drug holding part being placed on a front side of the electrode; and
   a cellulose resin film selected from the group consisting of regenerated cellulose, cellulose ester, cellulose ether, and cellulose nitrate and placed on a front side of the drug holding part,
   wherein the positively charged drug ions are administered through the cellulose resin film; and wherein the cellulose resin film is filled with an ion-exchange resin with a cation exchange group introduced thereto.

2. An iontophoresis device, comprising an active electrode structure comprising:
   an electrode to which a positive electrical potential is applied;
   a drug holding part for holding a drug solution containing positively chanted drug ions, the drug holding part being placed on the front side of the electrode; and
   a cellulose resin film selected from the group consisting of regenerated cellulose, cellulose ester, cellulose ether, and cellulose nitrate and placed on a front side of the drug holding part,
   wherein the positively charged drug ions are administered through the cellulose resin film, and wherein:
   the active electrode structure further comprising an electrolyte solution holding part for holding an electrolyte solution in contact with the electrode, and an anion exchange membrane placed on a front side of the electrolyte solution holding part; and
   the drug holding part is placed on a front side of the anion exchange membrane.

3. An iontophoresis device, comprising an active electrode structure comprising:
   an electrode to which a positive electrical potential is applied;
   a drug holding part for holding a drug solution containing positively charged drug ions, the drug holding part being placed on a front side of the electrode; and
   a cellulose resin film selected from the group consisting of regenerated cellulose, cellulose ester, cellulose ether, and cellulose nitrate and placed on a front side of the drug holding part, wherein the are administered through the cellulose resin film,
   a counter electrode structure, comprising:
   a second electrode to which a negative electrical potential is applied;
   a second electrolyte solution holding part for holding an electrolyte solution in contact with the second electrode;
   a second cation exchange membrane placed on a front side of the second electrolyte solution holding part;
   a third electrolyte solution holding part for holding an electrolyte solution, the third electrolyte solution holding part being placed on a front side of the second cation exchange membrane; and
   a second anion exchange membrane placed on a front side of the third electrolyte solution holding part.

4. An iontophoresis device, comprising an active electrode structure comprising:
   an electrode to which a positive electrical potential is applied;
   a drug holding part for holding a drug solution containing positively charged drug ions, the drug holding part being placed on a front side of the electrode; and
   a complex film composed of a cation exchange membrane and a cellulose-based resin film placed on a front side of the cation exchange membrane, the complex film being placed on a front side of the drug holding part,
   wherein the drug ions are administered through the cellulose-based resin film.

5. The iontophoresis device according to claim 4, wherein the cation exchange membrane has a porous structure filled with an ion-exchange resin.

6. The iontophoresis device according to claim 4, wherein a cation exchange group is introduced to the cellulose-based resin film.

7. The iontophoresis device according to claim 4, wherein the cellulose-based resin film is filled with an ion-exchange resin with a cation exchange group introduced thereto.

8. The iontophoresis device according to claim 4, wherein:
   the active electrode structure further comprising an electrolyte solution holding part for holding an electrolyte solution in contact with the electrode, and an anion exchange membrane placed on a front side of the electrolyte solution holding part; and
   the drug holding part is placed on a front side of the anion exchange membrane.

9. The iontophoresis device according to claim 4, further comprising a counter electrode structure, comprising:
   a second electrode to which a negative electrical potential is applied;
   a second electrolyte solution holding part for holding an electrolyte solution in contact with the second electrode;
   a second cation exchange membrane placed on a front side of the second electrolyte solution holding part;
   a third electrolyte solution holding part for holding an electrolyte solution, the third electrolyte solution holding part being placed on a front side of the second cation exchange membrane; and
   a second anion exchange membrane placed on a front side of the third electrolyte solution holding part.

10. The iontophoresis device according to claim 4, wherein an interface of the cation exchange membrane and the cellulose-based resin film are bonded, whereby the cation exchange membrane is integrated with the cellulose-based resin film.

11. The iontophoresis device according to claim 10, wherein the cation exchange membrane has a structure in which a pore of a porous film is filed with an ion-exchange resin.

12. The iontophoresis device according to claim 10, wherein a cation exchange group is introduced to the cellulose-based resin film.

13. The iontophoresis device according to claim 10, wherein:
- the active electrode structure further comprising an electrolyte solution holding part for holding an electrolyte solution in contact with the electrode, and an anion exchange membrane placed on the a front side of the electrolyte solution holding part; and
- the drug holding part is placed on a front side of the anion exchange membrane.

14. The iontophoresis device according to claims 10, further comprising a counter electrode structure, comprising:
- a second electrode to which a negative electrical potential is applied;
- a second electrolyte solution holding part for holding an electrolyte solution in contact with the second electrode;
- a second cation exchange membrane placed on a front side of the second electrolyte solution holding part;
- a third electrolyte solution holding part for holding an electrolyte solution, the third electrolyte solution holding part being placed on a front side of the second cation exchange membrane; and
- a second anion exchange membrane placed on a front side of the third electrolyte solution holding part.

15. The iontophoresis device according to claim 10, wherein:
- a surface of the cation exchange membrane facing the cellulose-based resin film is roughened; and
- the interface are bonded by any one of adhesion with an adhesive, a cross-linking reaction with a cross-linker, and formation of the cellulose-based resin film on the cation exchange membrane.

16. The iontophoresis device according to claim 15, wherein the cation exchange membrane has a porous structure filled with an ion-exchange resin.

17. The iontophoresis device according to claim 15, wherein a cation exchange group is introduced to the cellulose-based resin film.

18. The iontophoresis device according to claim 15, wherein the cellulose-based resin film is filled with an ion-exchange resin with a cation exchange group introduced thereto.

19. The iontophoresis device according to claim 15, wherein:
- the active electrode structure further comprising an electrolyte solution holding part for holding an electrolyte solution in contact with the electrode, and an anion exchange membrane placed on a front side of the electrolyte solution holding part; and
- the drug holding part is placed on a front side of the anion exchange membrane.

20. The iontophoresis device according to claim 15, further comprising a counter electrode structure, comprising:
- a second electrode to which a negative electrical potential is applied;
- a second electrolyte solution holding part for holding an electrolyte solution in contact with the second electrode;
- a second cation exchange membrane placed on a front side of the second electrolyte solution holding part;
- a third electrolyte solution holding part for holding an electrolyte solution, the third electrolyte solution holding part being placed on a front side of the second cation exchange membrane; and
- a second anion exchange membrane placed on a front side of the third electrolyte solution holding part.

21. The iontophoresis device according to claim 4, wherein a cation exchange group is introduced to the cellulose-based resin film.

22. The iontophoresis device according to claim 21, wherein the cellulose-based resin film is filled with an ion-exchange resin with a cation exchange group introduced thereto.

23. The iontophoresis device according to claim 21, wherein:
- the active electrode structure further comprises an electrolyte solution holding part for holding an electrolyte solution in contact with the electrode, and an anion exchange membrane placed on a front side of the electrolyte solution holding part; and
- the drug holding part is placed on a front side of the anion exchange membrane.

24. The iontophoresis device according to claim 21, further comprising: a counter electrode structure comprising:
- a second electrode to which a negative electrical potential is applied;
- a second electrolyte solution holding part for holding an electrolyte solution in contact with the second electrode;
- a second cation exchange membrane placed on a front side of the second electrolyte solution holding part;
- a third electrolyte solution holding part for holding an electrolyte solution, the third electrolyte solution holding part being placed on a front side of the second cation exchange membrane; and
- a second anion exchange membrane placed on a front side of the third electrolyte solution holding part.

* * * * *

UNITED STATES PATENT AND TRADEMARK OFFICE
CERTIFICATE OF CORRECTION

PATENT NO. : 7,660,626 B2
APPLICATION NO. : 11/195364
DATED : February 9, 2010
INVENTOR(S) : Akihiko Tanioka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 898 days.

Column 15, Line 36
"placed on the front side of the electrode" should read --placed on a front side of the electrode--.

Column 15, Line 61
"wherein the are administered through" should read --wherein the positively charged drug ions are administered through--.

Signed and Sealed this

Twenty-sixth Day of October, 2010

David J. Kappos
*Director of the United States Patent and Trademark Office*